United States Patent [19]
DiFrank et al.

[11] Patent Number: 5,988,951
[45] Date of Patent: Nov. 23, 1999

[54] PNEUMATIC GRAIN SAMPLE TRANSPORT SYSTEM

[76] Inventors: Gregory DiFrank, 680 Havens Corners Rd., Gahanna, Ohio 43230; Jan M. Elzey, 6223 Brooksong Way, Blacklick, Ohio 43004; Bryan E. Krupp, 1411 Aniko Ave., Lewis Center, Ohio 43035

[21] Appl. No.: 09/111,327

[22] Filed: Jul. 7, 1998

[51] Int. Cl.⁶ .................................................. B65G 53/66
[52] U.S. Cl. ................................ 406/32; 406/21; 406/83; 406/112; 406/125; 406/188; 406/189; 141/98; 141/350
[58] Field of Search .................................. 141/1, 13, 98, 141/275, 277, 346, 348, 349, 350; 406/150, 178, 111, 110, 112, 125, 130, 148, 149, 177, 179, 180, 13, 15, 16, 21, 187, 188, 189, 83, 84, 32

[56] References Cited

U.S. PATENT DOCUMENTS

| | | | |
|---|---|---|---|
| 4,395,164 | 7/1983 | Beltrop et al. | 406/74 |
| 4,466,761 | 8/1984 | Beltrop et al. | 406/74 |
| 4,620,577 | 11/1986 | Nordenswan | 141/98 |

OTHER PUBLICATIONS

Kelly Tube Systems, 4 pages.

*Primary Examiner*—Henry J. Recla
*Assistant Examiner*—Peter deVore
*Attorney, Agent, or Firm*—MacMillan, Sobanski & Todd, LLC

[57] ABSTRACT

The present apparatus relates to a pneumatic transport system to transport samples of grain between a filling station in a grain handling and storage structure and a receiving station in an office or inspection laboratory.

14 Claims, 10 Drawing Sheets

PNEUMATIC GRAIN SAMPLE TRANSPORT SYSTEM

FIELD OF THE INVENTION

The present invention relates to a pneumatic grain sample transport system. More particularly, this invention relates to a pneumatic transport system to transport samples of grain between a filling station in a grain handling and storage structure and a receiving station in an office or inspection laboratory.

BACKGROUND OF THE INVENTION

Grain samples are extracted from a grain handling and storage structure of a type well known in the art for testing the quality of the grain contained in the structure. The heretofore known systems for grain sampling either blow grain directly through a pipeline from a grain handling and storage structure or drop the grain samples by gravity into a receiver station located directly below the grain handling and storage structure or manually sample the storage structure and hand deliver the sample for testing. It will be appreciated that blowing grain directly through a tube causes damage to the grain and cross contamination between various samples and dropping the grain directly from the grain handling and storage structure requires that the lab be located beneath the grain handling and storage structure in violation of federal guidelines for locating the lab away from the grain handling and storage structure. The manual sampling and delivery of grain is labor intensive and time consuming.

It is an object of the present invention is to provide a pneumatic grain transport system that is simple to operate. It is another object of the present invention to provide a pneumatic grain transport system that automatically samples grain from a handling and storage structure, loads the sample into a carrier, and then transports the sample in the carrier to an inspection lab without need for human intervention. It is another object of the present invention to provide a pneumatic transport system that utilizes a carrier that may be automatically filled with a grain sample. Another object of the present invention to provide a pneumatic grain transport system that does not damage the grain in the sample. Yet another object of the present invention is to provide a pneumatic grain transport system that maintains the sample integrity and avoids cross-mixing with grain from previous samples.

SUMMARY OF THE INVENTION

Briefly, there is provided a pneumatic transport system to transport samples of grain along a pipeline between a carrier filling station in a grain handling and storage structure and a receiving station in an office or inspection laboratory. The system includes a hopper assembly including a surge hopper and an isolation hopper and having interposed there between a sample surge gate and positioned below the isolation hopper a sample isolation gate, a carrier having a first end and a second end, the first end of the carrier including a self-closing, spring biased door for automatic filling of the carrier in the carrier filling station, the second end of the carrier including an end-cap that may be manually removed to empty the contents of the carrier at the receiving station, a carrier filling station including a carrier filling assembly having a transport line, cushion assembly and a carrier clamp assembly, the transport line in communication with the pipeline and extending the length of the carrier filling station, the transport line including longitudinal slots to allow for pressurization of the pipeline from a blower and to guide the cushion assembly for decelerating the travel of the carrier and openings to operatively receive the carrier clamp assembly, the carrier clamp assembly including piston members having parallel extending rods and a perpendicular interconnecting yoke attached thereto, the carrier clamp assembly includes pivotable locking arms to hold the carrier firmly against the bottom of the yoke during filling of the carrier, a receiving station to receive the carrier when the carrier is moved from the carrier filling station; and a pipeline operatively interconnecting the carrier filling station and the receiving station.

A method of pneumatically transporting samples of grain along a pipeline between a carrier filling station in a grain handling and storage structure and a receiving station in an office or inspection laboratory is also disclosed. The method comprising the steps of filling a hopper assembly including a surge hopper and an isolation hopper and having interposed there between a sample surge gate and positioned below the isolation hopper a sample isolation gate with grain, automatically filling a carrier with the grain from the hopper at the carrier filling station, the carrier filling station including a carrier filling assembly having a transport line, cushion assembly and a carrier clamp assembly, the transport line in communication with the pipeline and extending the length of the carrier filling station, the transport line including longitudinal slots to allow for pressurization of the pipeline from a blower and to guide the cushion assembly for decelerating the travel of the carrier and openings to operatively receive the carrier clamp assembly, the carrier clamp assembly including piston members having parallel extending rods and a perpendicular interconnecting yoke attached thereto, the carrier clamp assembly includes pivotable locking arms to hold the carrier firmly against the bottom of the yoke during filling of the carrier; and transporting the carrier to the receiving station through a pressurized pipeline.

BRIEF DESCRIPTION OF THE DRAWINGS

Further features and objects of the present invention will become apparent from the following description made with reference to the figures in which.

DETAILED DESCRIPTION OF THE PREFERRED EMBODIMENTS

Figure 1:
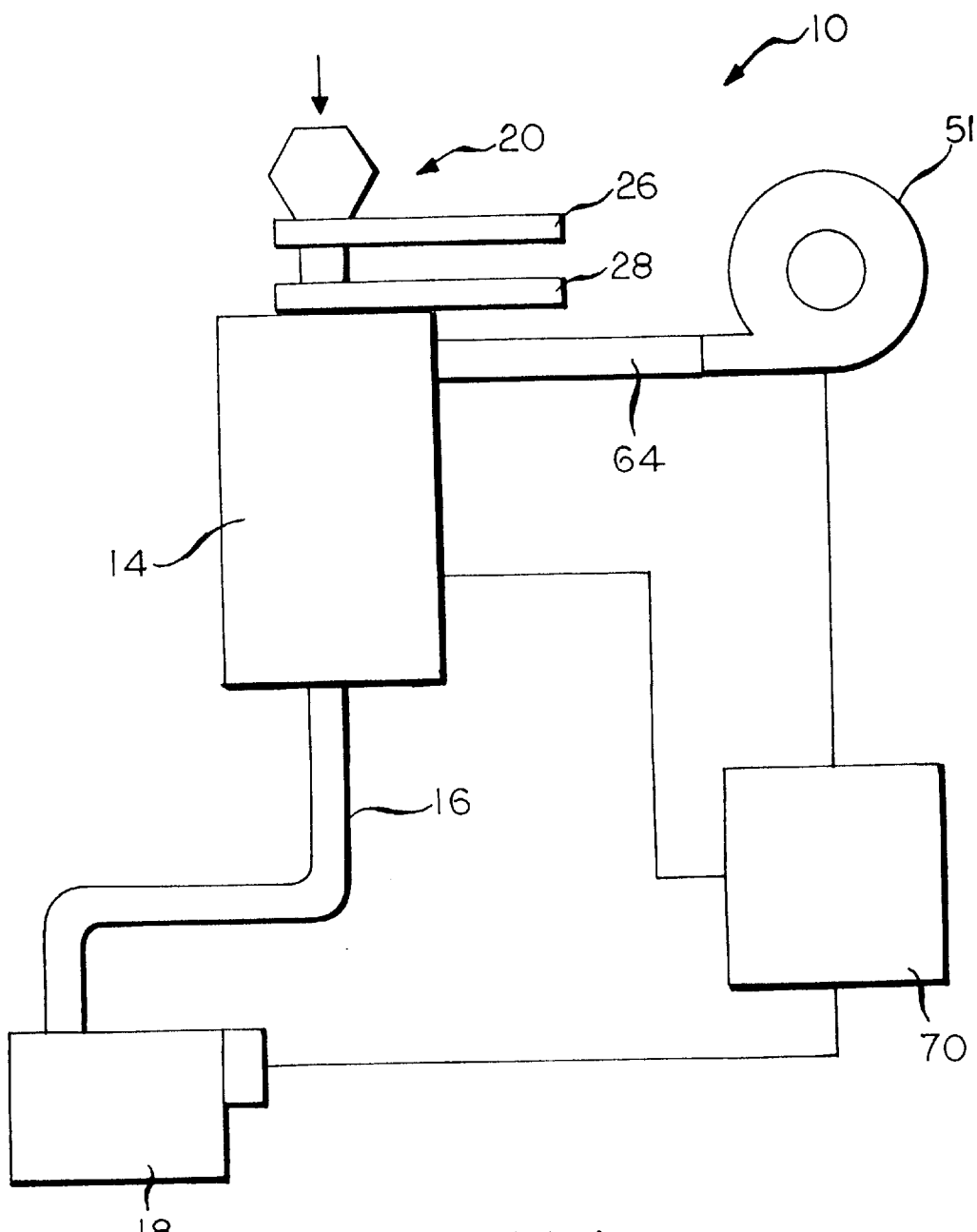
FIG. 1 is a schematic of the pneumatic transport system in accordance with the present invention.
Figure 2:
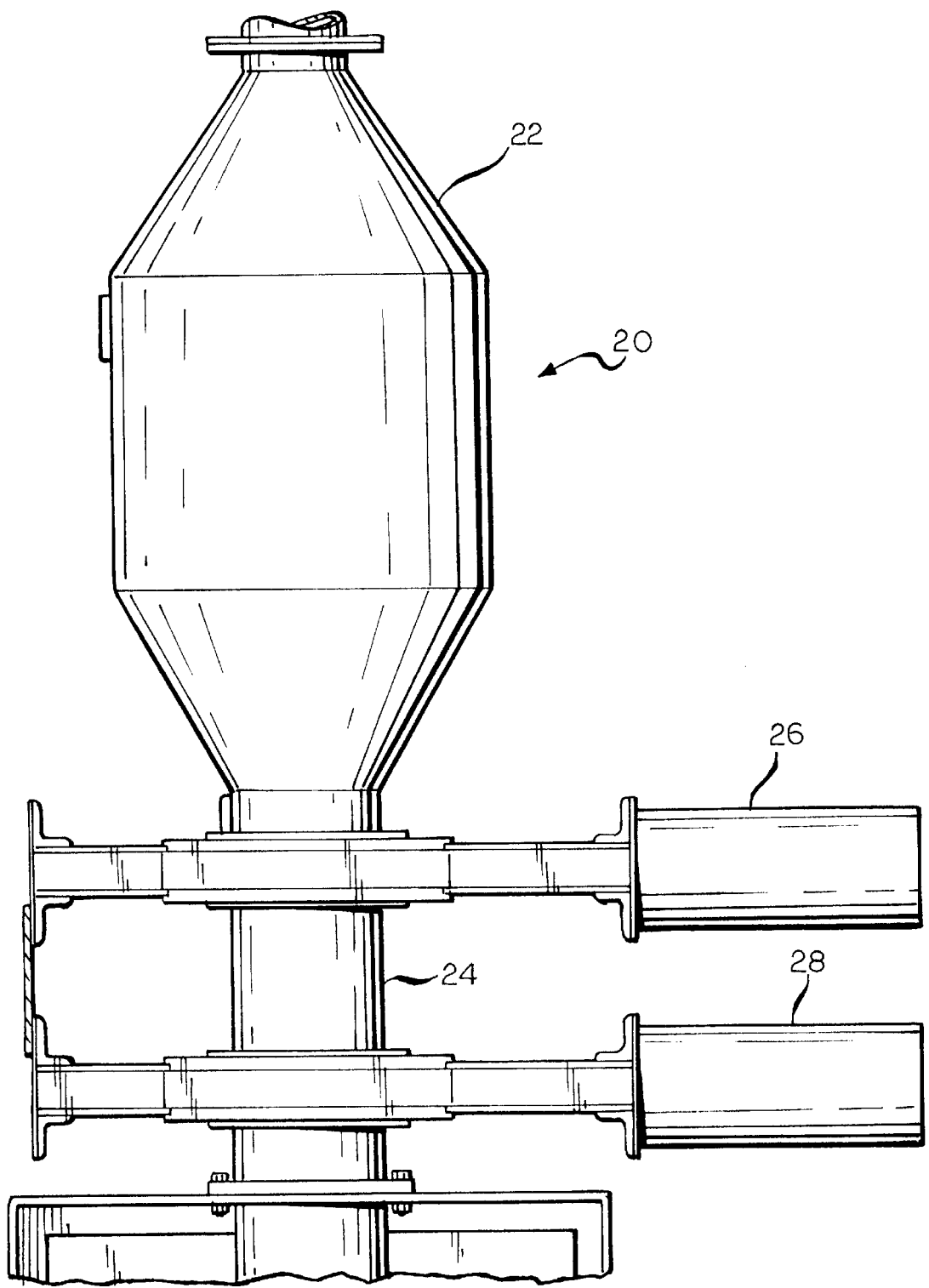
FIG. 2 is an enlarged partial front view of the hopper assembly of the pneumatic transport system of FIG. 1.
Figure 3:
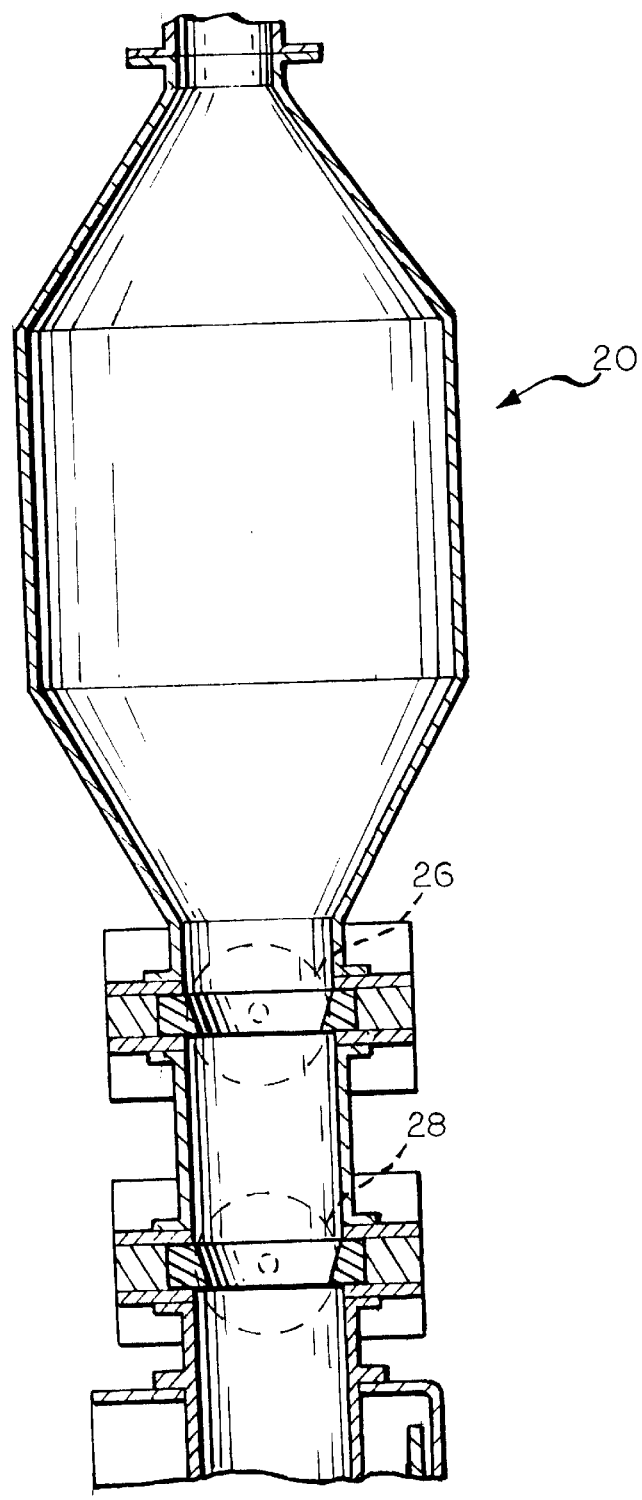
FIG. 3 is an enlarged partial cross-sectional view of the hopper assembly.
Figure 4:
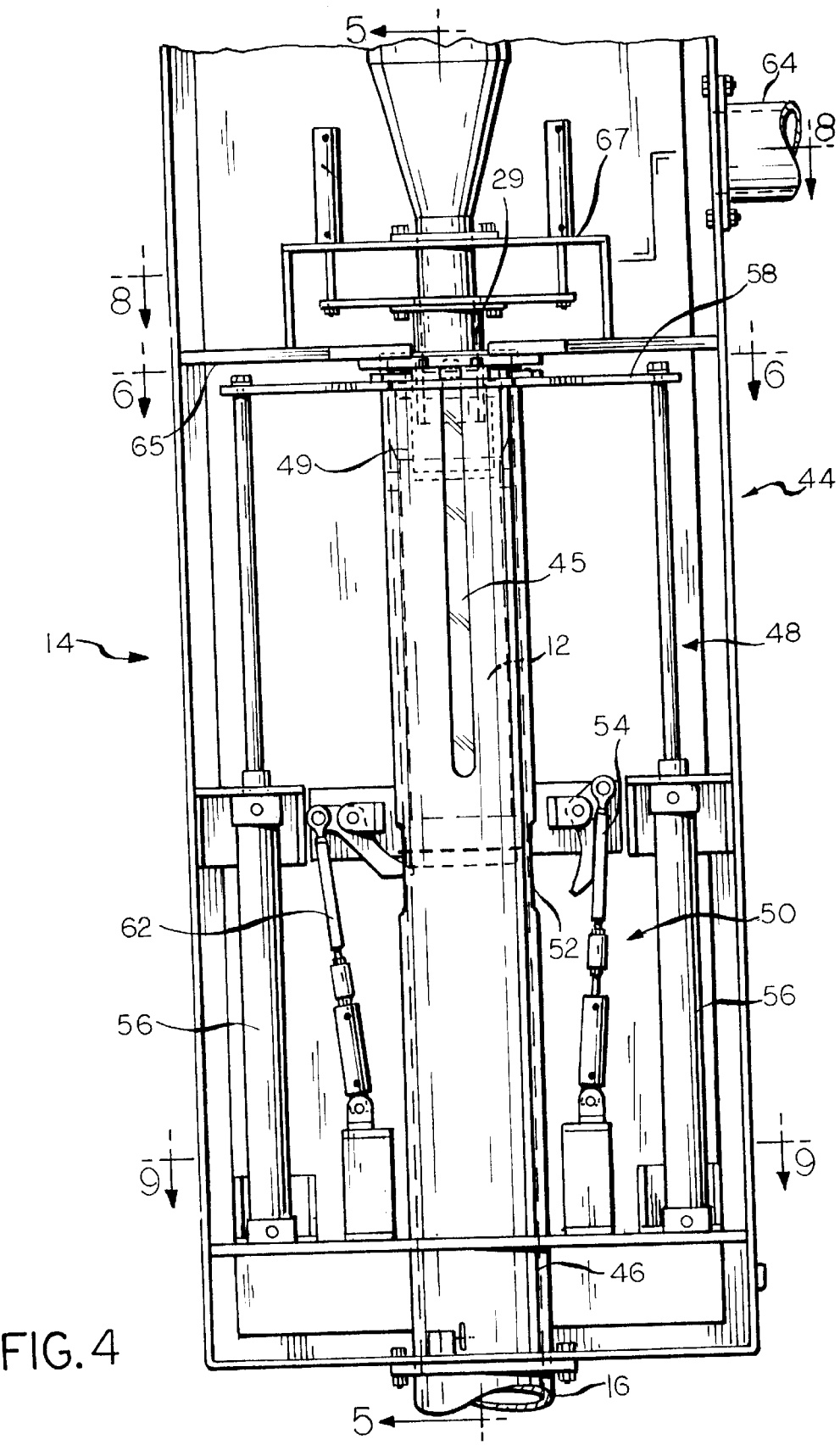
FIG. 4 is an enlarged cross-sectional view of the carrier filling station.
Figure 5:
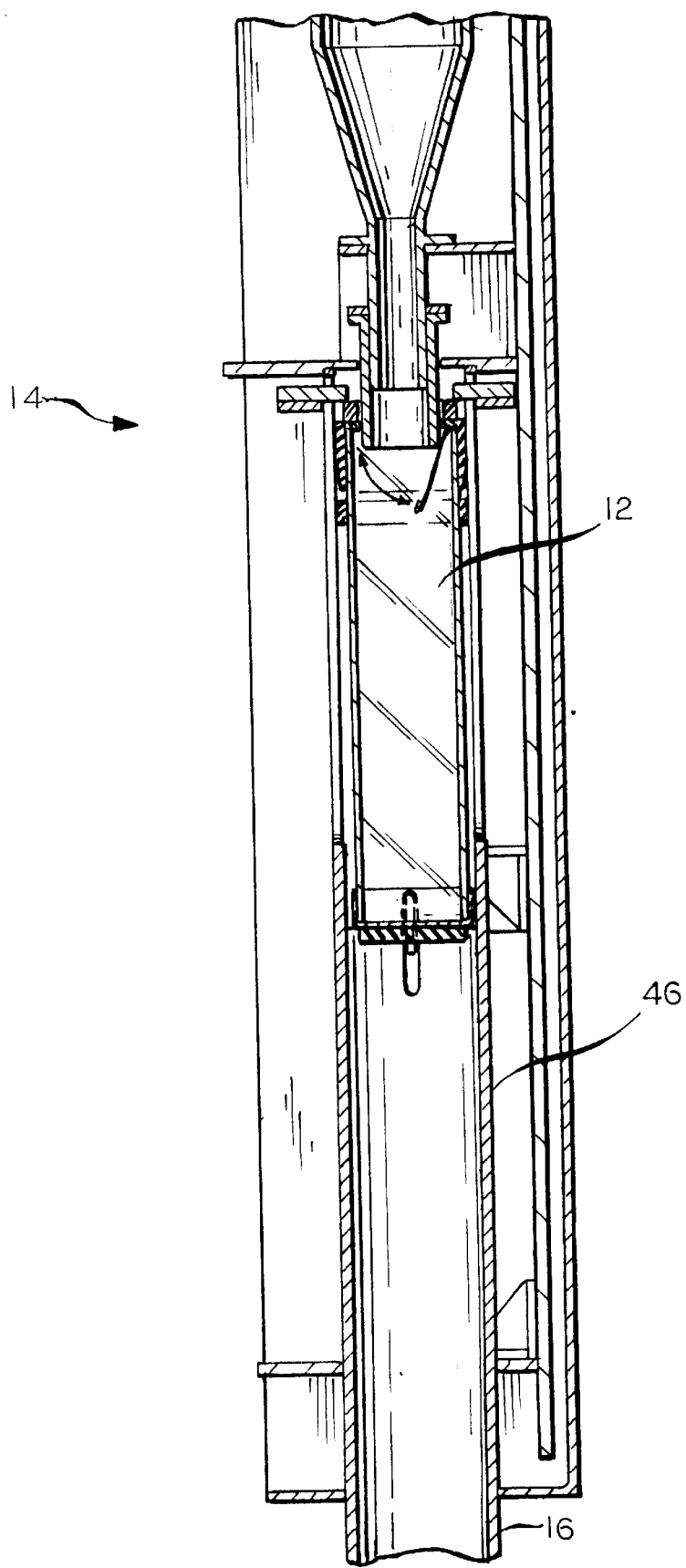
FIG. 5 is an enlarged cross-sectional view of the carrier filling station including a carrier to receive a sample.
Figure 6:
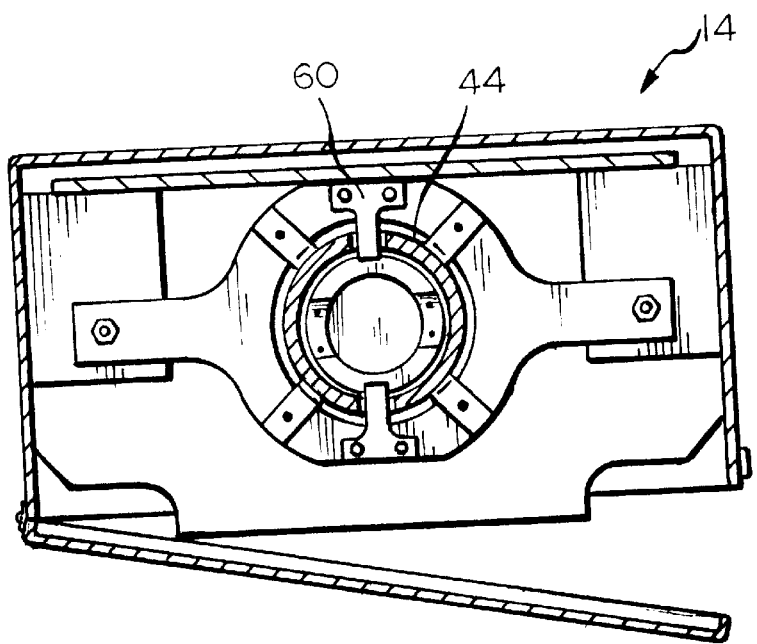
FIG. 6 is an enlarged top view of the carrier filling station.
Figure 7:
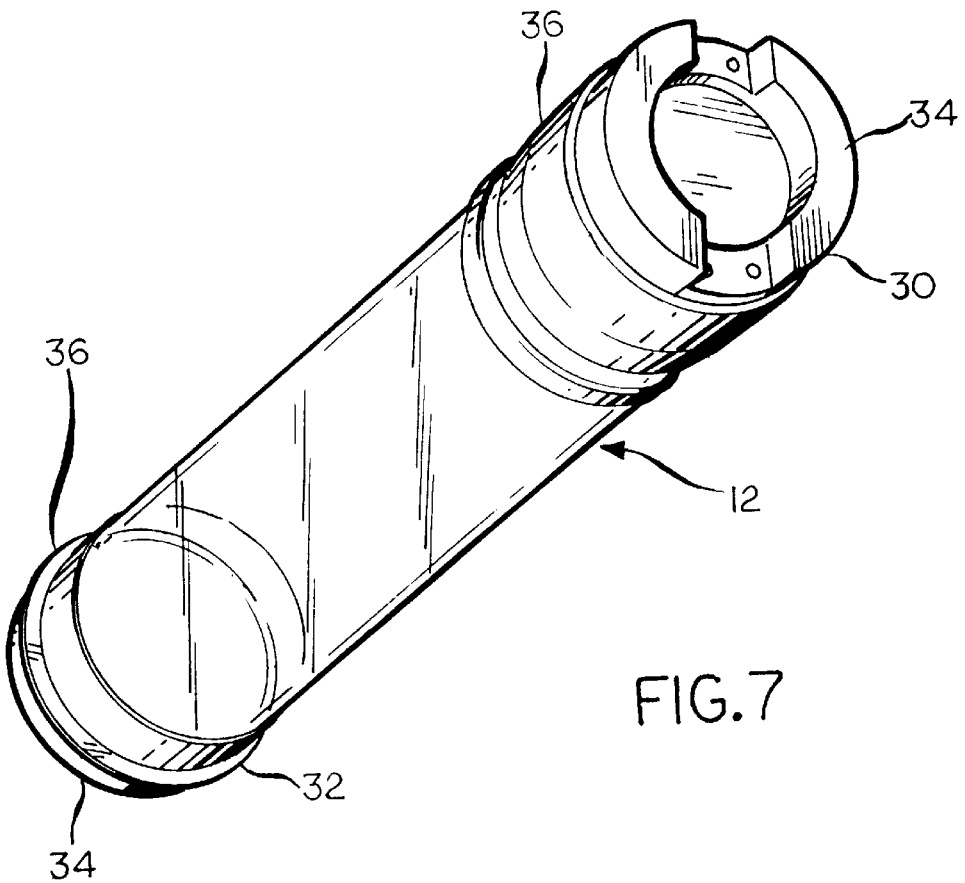
FIG. 7 is a perspective view of the carrier.
Figure 8:
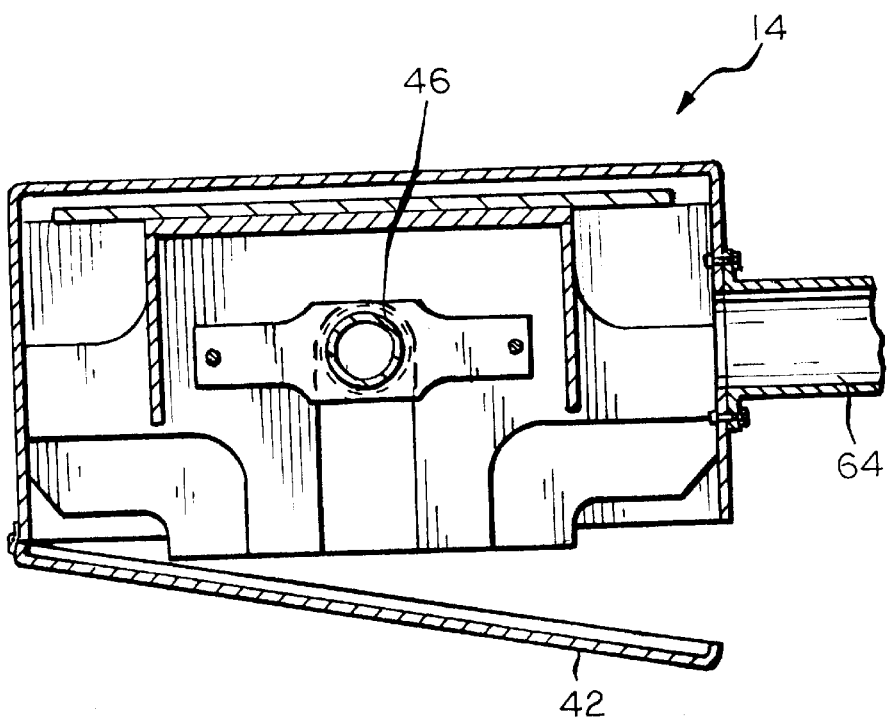
FIG. 8 is a cross-sectional view of the carrier filling station taken along line x—x.
Figure 9:
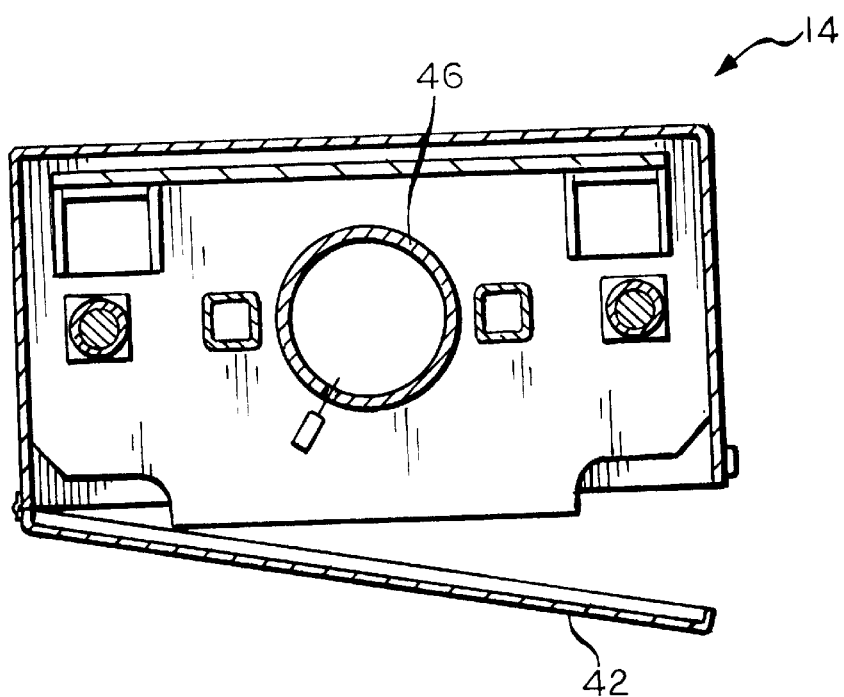
FIG. 9 is a cross-sectional view of the carrier filling station taken along line z—z.
Figure 10:
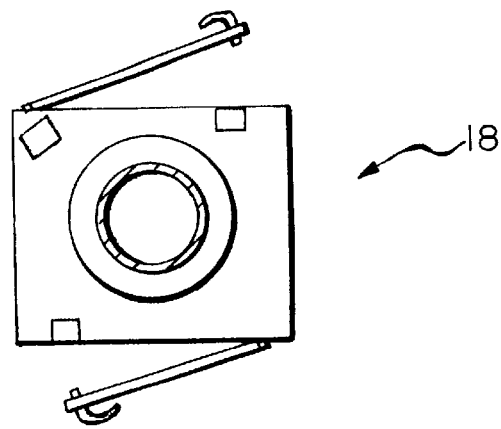
FIG. 10 is a cross sectional view of the receiving station.
Figure 11:
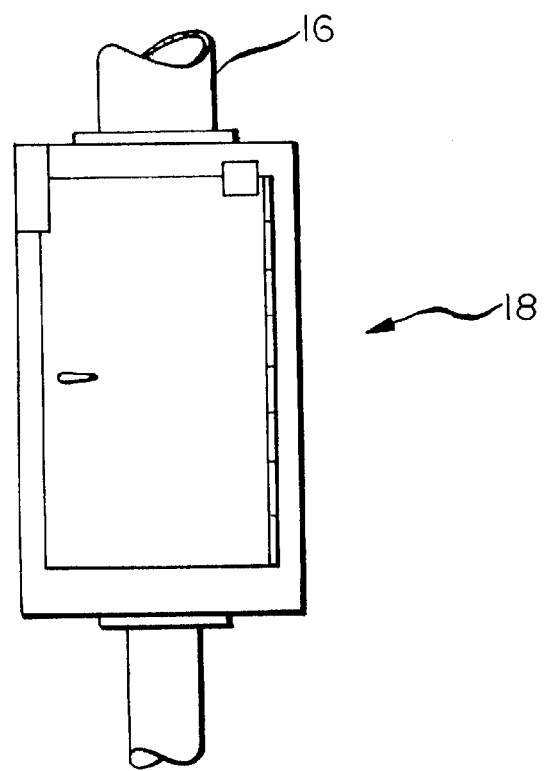
FIG. 11 is a front view of the receiving station.
Figure 12:
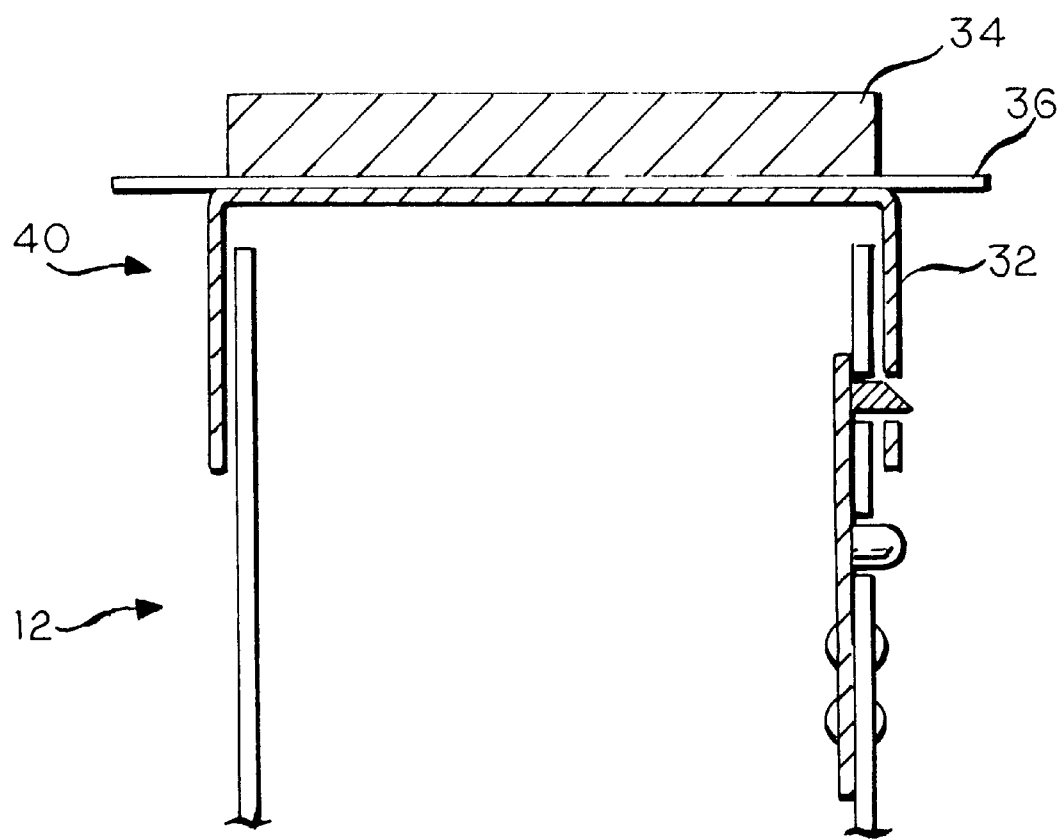
FIG. 12 is a partial cross sectional view of the sample carrier removable cap.
Figure 13:
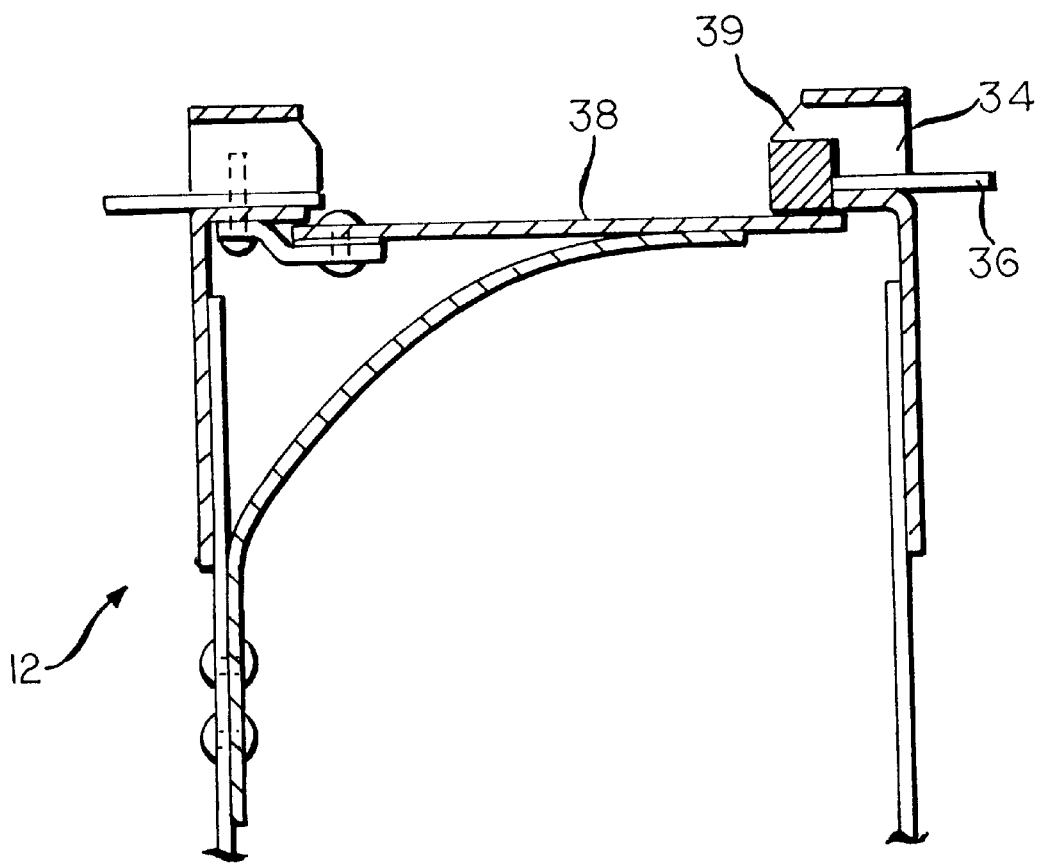
FIG. 13 is a partial cross sectional view of the sample carrier door.

Referring to the figures wherein like reference characters represent like elements, there is shown a pneumatic grain sample transport system 10 in accordance with the present invention. In considering the figures, it will be appreciated that for purposes of clarity certain details of construction are not provided in view of such details being conventional and well within the skill of the art based upon the specific operating requirements of the pneumatic grain transport system once the invention is disclosed and explained. For example, slide gates, sensors, detectors and the like may be added to the pneumatic grain sample transport system as necessary. Reference is made to Perry and Chilton, CHEMICAL ENGINEERS' HANDBOOK, 5th Edition, McGraw Hill, N.Y., 1973, and to the pneumatic transport industry literature generally for detailed descriptions of the various process control apparatus and conditions.

The pneumatic grain sample transport system 10 automatically samples grain from a handling and storage structure (not shown), loads the sample into a carrier 12 in a carrier filling station 14 and then transports the sample in the carrier via a pipeline 16 to a receiving station 18. It will be appreciated that the grain is typically stored in a handling and storage structure such as a silo of a type well known in the art before the grain is shipped or exported. It will be further appreciated that before any grain can be exported from the United States, the grain must first be certified by the Federal Grain Inspection Service (FGIS) in a laboratory as having met a specific standard. The present invention facilitates testing of grain stored in handling and storage structures without damaging the grain or commingling different grain samples and without requiring manual sampling.

The pneumatic grain sample transport system 10 includes a hopper assembly 20 that is fed with sample grain from a sampler system (not shown) such as a cross cut sampler system commercially available from Intersystems, Inc. The hopper assembly 20 includes a surge hopper 22 operatively connected to an isolation hopper 24. Interposed between the surge hopper 22 and the isolation hopper 24 is a sample surge gate 26 and positioned downstream of the isolation hopper is a sample isolation gate 28. Operatively attached downstream of the sample isolation gate 28 is a telescoping spout 29. The spout 29 extends and retracts by actuating pistons 31 within carrier 12 to feed grain and the like into the carrier. The gates 26 and 28 are commercially available slide gates of a type well known in the art to cooperatively meter grain from the surge hopper 22 to the isolation hopper 24 and to the carrier filling station. It will be appreciated that the volume between the two slide gates 26 and 28 matches the volume of the carrier 12. When the volume within the isolation hopper 24 between the slide gates 26 and 28 is filled with sample grain from the surge hopper 22, the upper sample surge gate 26 closes and the upper surge hopper 22 continues to fill with grain.

The sample grain is transported in the carrier 12 from the carrier filling station 14 to the receiving station 18 along a pipeline 16. The carrier 12 is a cylindrical container having a first end 30 and a second end 32. The carrier 12 may be made of most any suitable material and of most any suitable size to transport the sample within the confines of the pipeline 16. In a preferred embodiment, the carrier 12 is about 24 inches long and about 5.25 inches diameter and made of a clear plastic material and holds about 2500 grams of grain such as corn and the like.

The first end 30 of the carrier 12 and the second end 32 of the carrier include end cushions 34 to cushion the impact of the carrier against the carrier filling station 14 and the receiving station 18 and gaskets 36 to seal the carrier against the sidewalls of the pipeline 16. The end cushions 34 and gaskets 36 may be formed of most any suitable elastomeric material. The first end 30 of the carrier 12 includes a self-closing, spring biased door 38 having a magnetic catch 39 that is used for automatic filling of the carrier in the carrier filling station 14 as more fully described herein. The second end 32 of the carrier 12 includes a positive latching, end-cap 40 that may be manually removed to empty the contents of the carrier at the receiving station 18.

The carrier 12 transports the grain sample between the carrier filling station 12 and the receiving station 18 within the pipeline 16. The pipeline 16 is of a uniform cross-section and can be constructed from various curved linear segments respectively joined by suitable means such as a sleeve or metal coupler band of a type will known in the art (not shown). The pipeline 16 can extend over considerable lateral distances as well as over different vertical distances. Each terminus of the pipeline 16 is associated with the carrier filling station 14 and the receiving station 18, respectively. In a preferred embodiment, the pipeline 16 is a 6 inch diameter rigid metal tubing. It will be appreciated that due to the length of the carrier 12, the minimum bend radius of the pipeline 16 is approximately 5 feet.

The carrier filling station 14 is an airtight enclosure having a hinged door 42 that provides access to the interior of the enclosure. Positioned within the enclosure is a carrier filling assembly 44. The carrier filling assembly 44 includes a transport line 46, cushion assembly 48 and a carrier clamp assembly 50. The transport line 46 includes a transport alignment ring 49 having a conical shape to facilitate alignment of the carrier 12 with the spout 29. The transport line 46 extends the length of the carrier filling station 14 from the pipeline 16 to the spout 29. The transport line 46 includes two opposing longitudinal slots 48 to allow for pressurization of the pipeline 16 from a blower 51 and guide the cushion assembly 48 to decelerate the travel of the carrier 12 and two openings 52 to receive carrier clamps 54 of the carrier clamp assembly 50. The cushion assembly 48 includes two spaced piston members 56 having parallel extending rods and a perpendicular interconecting yoke 58. Attached to the yoke 58 are T-shaped tabs 60 which travel within the longitudinal slots 45. The carrier clamp assembly 50 holds the carrier 12 firmly against the bottom of the yoke 58 during filling of the carrier. The carrier clamp assembly 50 includes two opposing pneumatically pivotable locking arms 62. As the carrier 12 is drawn upward within the transport line 46, the first end 30 of the carrier contacts the tabs 60 thereby decelerating the carrier to a resting position. Sensors detect the carrier in the resting position and extend the telescoping spout 29 against the door 78 opening the door and cause the locking arms 62 to pivot inwardly underneath of the second end 32 of the carrier 12 thereby locking the carrier in position for filling with sample grain.

After the carrier 12 is locked in position, the bottom isolation gate 28 opens dispensing all of the sample grain from the isolation hopper 24 into the carrier. After the sample grain is emptied into the carrier 12, the locking arms 62 release from underneath of the second end 32 of the of the carrier and the T-shaped tabs 60, biased by the piston members 56, urge the carrier away from the spout 29 thereby closing the spring biased door 38. Simultaneously, with the movement of the carrier 12 away from the spout 29, the blower 51 is actuated to create a positive pressure within the enclosure thereby forcing the carrier from the filling station 14 through the pipeline 16 to the receiving station 18.

The blower 51 is a reversible blower to pneumatically convey the carrier 12 filled with grain from the filling station 14 to the receiving station 18. It will be appreciated that during blower operation, the entire carrier filling station 14 is pressurized (or evacuated) by the blower 51 through blower supply line 64. This is required for operation since the spout 29 is inside the uppermost portion of the transport line 46 thereby forming an airtight seal. In a preferred embodiment, the blower supply line 64 is a 4" metal tubing that is installed between the blower 51 and the carrier filling station 14. Since the blower 51 is reversible, only one transport line into the carrier filling station 14 is required. The blower 51 is used to create the pressure (and vacuum) needed to drive the carrier 12 through the pipeline 16.

The receiving station 18 is a cushioned receptacle that is used to receive the carrier 12 when the carrier is moved from the carrier filling station 14. The receiving station 18 is of a commercially available design such as typically utilized in the pneumatic transport industry. In a preferred embodiment, the receiving station is generally located within an office building or laboratory for evaluation of the grain samples. The receiving station 18 is an airtight enclosure having an access door for access to and removal of the carrier 12 as desired. The enclosure includes a sensor 66 mounted within the enclosure to signal when the carrier 12 is present and a pressure relief valve 68 to vent internal air pressure or allow air into the enclosure as required.

The pneumatic grain sample transport system 10 operation is controlled by a Programmable Logic Controller (PLC) 70. The PLC 70 is in communication with the necessary components to interface with the associated field and operator control devices and for interfacing with all automatic carrier filling station assembly sensors, receiving box sensors, solenoid conductors, motor control wiring, and switches as well known in the art.

The carrier 12 transport is initiated by a signal from an operator. The system 10 will normally be selected for "Automatic" mode and in an "Idle" state with the carrier 12 sitting in the home position in the receiving station 18. A "Sampling On Signal" will initialize system 10 and indicate that a shipping operation or a receiving operation is desired and the system will respond by calling the carrier 12 to the filling station 14 for filling. While the carrier 12 is in route to the filling station 14 the sample surge gate 26 will be energized to open a flow path between the surge hopper 22 and the isolation hopper 24. The sampler will operate through a PLC, approximately every 30 seconds, and begin taking samples of each draft of a bulk weigher of a type well known in the art. As the sampler operates, the sample material will flow through the existing divider box, then into the sample surge hopper 22 and into the sample isolation hopper 24.

While the isolation hopper 24 is filling, the PLC will accumulate the number of drafts and samples and compare this accumulated value to an entered set point. When the accumulated value is greater than or equal to the set point, the system will signal to fill the carrier 12 and send it to the receiving station 18, this signal will be identified as "Send Sample". In the event that the isolation hopper 24 is filled before the "Send Sample" signal is sent from the PLC, the sample surge gate 26 will be de-energized to close the flow of material into the isolation hopper and the sample isolation gate 28 will be energized to begin filling the carrier 12. While the carrier 12 is filling, the sample material will continue to fill the surge hopper 22. After the carrier 12 is loaded and sent on its way to the receiving station 18 the sample surge gate 26 will be energized again to begin filling the isolation hopper. The above operation will be repeated three times when the system is in the shipping mode of operation. In a preferred embodiment, two cycles will be necessary in order to fulfill the requirements of two full sample carriers for each shipping bin, and one cycle will be necessary to purge the surge hopper 22 of any remaining material that exists before the next shipping bin is filled.

When the system 10 is in the receiving mode, the above operation will be repeated approximately 3 times for each shipment. Two cycles will be necessary for the lab and one cycle to purge the surge hopper 22.

It will be appreciated that ultimately the number of cycles needed, in either the shipping or receiving mode, will be a number that enables the transport of the necessary amount of sample material for evaluation. Accordingly, it will be necessary for individual components of the system 10 to be adjusted to accommodate the required amounts to ensure the overall efficiency and requirements of the system are achieved.

When the "Sampling On" signal is received, the blowers' 51 reversing starter will be energized in the vacuum direction to pull the carrier 12 into the filling station 14. The carrier 12 will enter the enclosure and make contact with the cushion yoke 58. This contact will cause the cushion piston members 56 to extend slowly until the carrier 12 reaches a home limit switch 65. With the home limit switch 65 is closed, the carrier clamps 54 lock the carrier 12 into position. With the home switch closed 65 the blower 51 is de-energized.

With the carrier 12 in the home position, a telescoping spout solenoid 67 will be energized to extend the spout 29 into the carrier. A position limit switch will close to indicate that the spout 29 is fully extended into the carrier 12. With the spout 29 fully extended the sample surge gate 26 will be de-energized to stop the flow of material into the isolation hopper 24 and the isolation gate 28 will be energized to begin filling the carrier 12 with grain sample. After the isolation gate 28 is opened a small time delay will expire before this gate is cycled closed again and the sample surge gate 26 is re-opened. Shortly after the gates change position, the telescoping spout solenoid 67 will de-energize to extract the spout 29 from the carrier 12.

In automatic mode, transit of the carrier 12 is controlled by the PLC 70. All the operator has to do is replace the carrier 12 into the receiving station 18 as soon as it is emptied. The PLC 70 will automatically run through the number of trips required for the required sample amount, and the PLC will add another trip for a clean cycle. As long as the operator always replaces the sample carrier 12, the system will be ready for taking samples and transporting them.

When a "Send Sample" signal is received from the PLC 70 or a manual signal is sent, the blowers' 51 reversing starter will be energized in the pressure direction to push the carrier 12 into the receiving station 18. The carrier 18 will enter the enclosure and make contact with a proximity sensor that will detect when the carrier 12 has reached the home position. This contact will cause the blower 51 to de-energize and a signal will notify the operator that the carrier 12 is in the home position.

Mode selection of the system 10 will be controlled through the PLC 70. The system 10 can be changed from "Automatic" to "Manual" through activation of the PLC 70 as previously described. When the sample transport station is selected for manual mode operation, the system 10 waits for manual input signals from an operator.

The patents and documents referenced herein are hereby incorporated by reference.

Numerous characteristics and advantages of the invention have been set forth in the foregoing description. It will be understood, of course, that this disclosure is, in many respects, only illustrative. Changes can be made in details, particularly in matters of shape, size, and arrangement of parts without exceeding the scope of the invention.

Having described presently preferred embodiments of the invention, the invention may be otherwise embodied within the scope of the appended claims.

What is claimed is:

1. A pneumatic transport system to transport samples of grain along a pipeline between a carrier filling station in a grain handling and storage structure and a receiving station in an office or inspection laboratory, the system comprising:

a hopper assembly including a surge hopper and an isolation hopper and having interposed there between a sample surge gate and positioned below the isolation hopper a sample isolation gate;

a carrier having a first end and a second end, the first end of the carrier including a self-closing, spring biased door for automatic filling of the carrier in the carrier filling station, the second end of the carrier including an end-cap that may be manually removed to empty the contents of the carrier at the receiving station;

a carrier filling station including a carrier filling assembly having a transport line, cushion assembly and a carrier clamp assembly, the transport line in communication with the pipeline and extending the length of the carrier filling station, the transport line including longitudinal slots to allow for pressurization of the pipeline from a blower and to guide the cushion assembly for decelerating the travel of the carrier and openings to operatively receive the carrier clamp assembly, the cushion assembly including piston members having parallel extending rods and a perpendicular interconnecting yoke attached thereto, the carrier clamp assembly includes pivotable locking arms to hold the carrier firmly against the bottom of the yoke during filling of the carrier;

a receiving station to receive the carrier when the carrier is moved from the carrier filling station; and a pipeline operatively interconnecting the carrier filling station and the receiving station.

2. A method pneumatically transporting samples of grain along a pipeline between a carrier filling station in a grain handling and storage structure and a receiving station in an office or inspection laboratory, the method comprising the steps of:

filling a hopper assembly including a surge hopper and an isolation hopper and having interposed there between a sample surge gate and positioned below the isolation hopper a sample isolation gate with grain;

automatically filling a carrier with the grain from the hopper at the carrier filling station, the carrier filling station including a carrier filling assembly having a transport line, cushion assembly and a carrier clamp assembly, the transport line in communication with the pipeline and extending the length of the carrier filling station, the transport line including longitudinal slots to allow for pressurization of the pipeline from a blower and to guide the cushion assembly for decelerating the travel of the carrier and openings to operatively receive the carrier clamp assembly, the cushion assembly including piston members having parallel extending rods and a perpendicular interconnecting yoke attached thereto, the carrier clamp assembly includes pivotable locking arms to hold the carrier firmly against the bottom of the yoke during filling of the carrier; and transporting the carrier to the receiving station through a pressurized pipeline.

3. A pneumatic transport system to transport a grain sample, the system comprising:

a carrier for transporting the grain sample;

a hopper assembly including a spout for metering the grain sample;

a carrier filling station in communication with the hopper assembly and adapted to automatically receive the grain sample and fill the carrier via the spout, the carrier filling station including a carrier filling assembly having a transport line in alignment with the spout extending a length of the carrier filling station, a cushion assembly for decelerating the travel of the carrier, and a carrier clamp assembly for holding the carrier during filling of the carrier; and a receiving station capable of receiving the carrier when the carrier is moved from the carrier filling station; and a pipeline operatively interconnecting the carrier filling station and the receiving station.

4. The transport system according to claim 3, wherein the carrier includes a first end and a second end, the first end of the carrier including a self-closing, spring-biased door for automatic filling of the carrier in the carrier filling station, the second end of the carrier including an end-cap that may be manually removed to empty the contents of the carrier at the receiving station.

5. The transport system according to claim 3, wherein the hopper assembly includes a surge hopper, an isolation hopper, a surge gate being interposed between the surge hopper and the isolation hopper, and an isolation gate, the isolation hopper being interposed between the surge gate and the isolation gate.

6. The transport system according to claim 3, wherein the transport line includes longitudinal slots to allow for pressurization of the pipeline from a blower.

7. The transport system according to claim 6, wherein the cushion assembly includes T-shaped tabs for travelling within the longitudinal slots of the transport line and contacting a first end of the carrier, thereby decelerating the travel of the carrier.

8. The transport system according to claim 3, wherein the cushion assembly includes piston members having parallel extending rods and a perpendicular interconnecting yoke attached thereto.

9. The transport system according to claim 8, wherein the carrier clamp assembly includes pivotable clamps for holding the carrier against the bottom of the yoke during filling of the carrier.

10. The transport system according to claim 9, wherein the spout is telescoping and extends into the carrier during filling of the carrier.

11. The transport system according to claim 3, further comprising a programmable logic controller for automatically controlling the travel of the carrier from the receiving station to the carrier filling station.

12. The transport system according to claim 11, wherein the programmable logic controller causes the hopper assembly to meter the grain sample while the carrier is traveling from the receiving station to the carrier filing station.

13. The transport system according to claim 12, wherein the programmable logic controller accumulates a number of grain samples and compares the accumulated number of grain samples to a set point, the carrier being filled when the accumulated value is greater than or equal to the set point.

14. The transport system according to claim 3, further comprising a programmable logic controller for manually controlling the travel of the carrier from the receiving station to the carrier filling station.

* * * * *